United States Patent [19]

Barnes et al.

[11] 4,138,322

[45] Feb. 6, 1979

[54] POLAROGRAPHIC APPARATUS

[75] Inventors: David Barnes, Caringbah; Champa H. Metters, Buckley, both of Australia

[73] Assignee: University of Strathclyde, Glasgow, Scotland

[21] Appl. No.: 815,024

[22] Filed: Jul. 12, 1977

[51] Int. Cl.² ............................................. G01N 27/34
[52] U.S. Cl. ................................................. 204/195 H
[58] Field of Search ......................... 204/195 H, 195 R

[56] References Cited

U.S. PATENT DOCUMENTS

| | | | |
|---|---|---|---|
| 2,500,284 | 3/1950 | Hetrovsky | 204/195 H |
| 3,410,763 | 11/1968 | Capuano | 204/195 H |
| 3,421,989 | 1/1969 | Haagen-Smit | 204/195 H |
| 3,871,985 | 3/1975 | Crippen et al. | 204/195 R |

FOREIGN PATENT DOCUMENTS 738632  8/1943  Fed. Rep. of Germany ...... 204/195 H

OTHER PUBLICATIONS

"Analytical Chemistry", vol. 28, No. 4, Apr. 1956, pp. 630, 636–637.
"Analytical Chemistry", vol. 26, No. 7, Jul. 1954, pp. 1121–1123.
"Analytical Chemistry", vol. 26, No. 8, Aug. 1954, pp. 1351–1354.
"Techlink", No. 1887, Feb. 24, 1976.
"Chemistry & Industry"; Jan. 17, 1948; pp. 37 & 38.

*Primary Examiner*—T. Tung
*Attorney, Agent, or Firm*—Finnegan, Henderson, Farabow & Garrett

[57] ABSTRACT

A polarographic analysis cell is described for analysis of a continuously flowing stream of liquid using a dropping mercury cathode technique. In a cell having an inlet and an outlet for throughflow of liquid, a shielded dropping mercury cathode is mounted, the cathode shield having the configuration of a funnel having an upper cup portion and a lower stem portion, the lower extremity of the stem terminating in a laterally-directed orifice which prevents entry into the shield of gas bubbles issuing from a gas diffuser also provided in the cell to diffuse deoxygenating inert gas into the cell during use.

9 Claims, 1 Drawing Figure

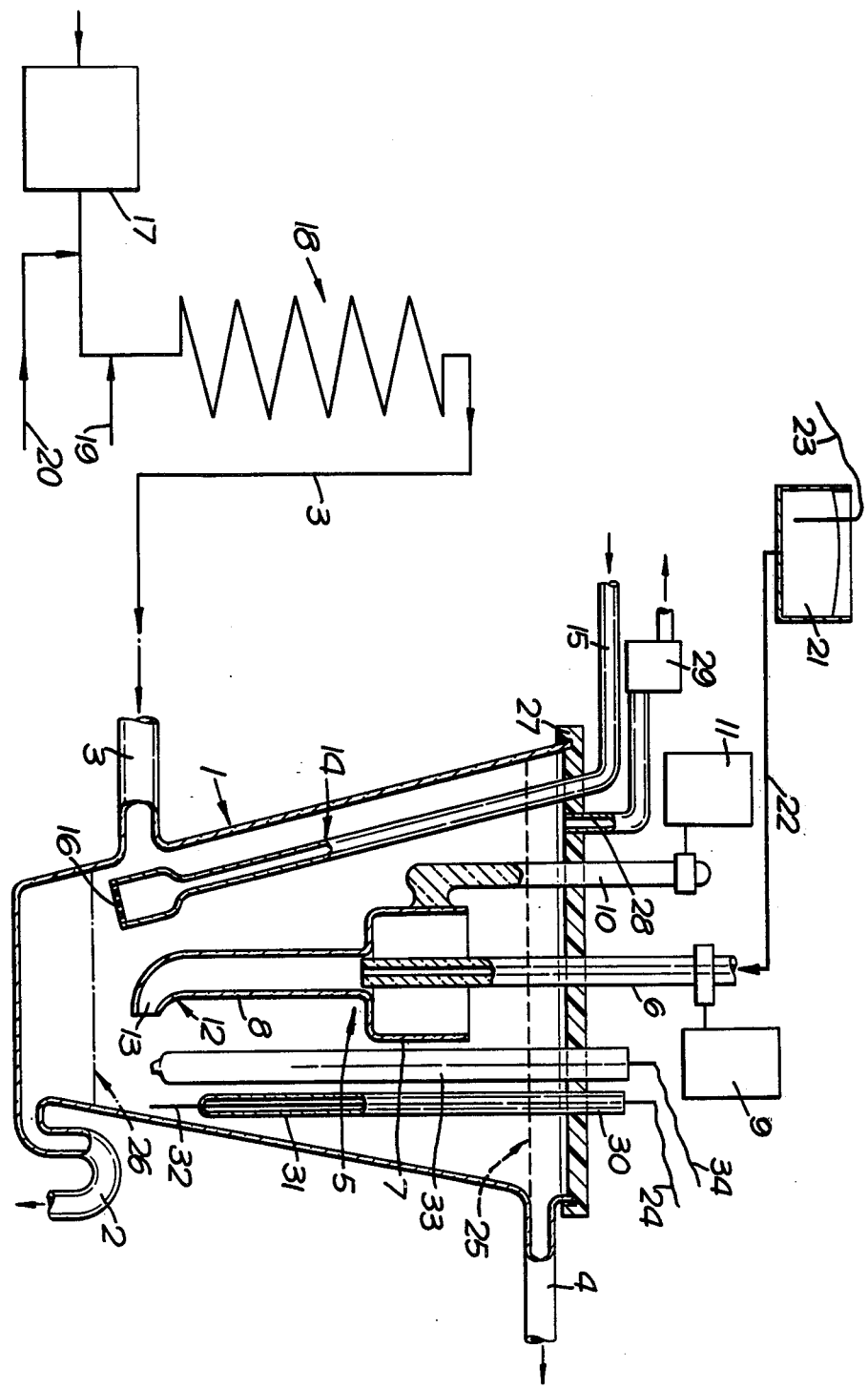

POLAROGRAPHIC APPARATUS

The present invention relates to the field of analytical chemistry and in particular to apparatus for use in the continuous polarographic analysis of a flowing stream of liquid. The invention provides apparatus for the polarographic determination of cationic species in effluent and is particularly suitable for the determination of such cations as copper, lead, cadmium and zinc.

Polarographic techniques which utilise a dropping mercury cathode are extremely sensitive to physical movement of the liquid under analysis. Conventionally, polarographic cells are mounted on anti-vibration tables to minimise interference from this source. It is extremely difficult to analyse flowing samples polarographically using a dropping mercury cathode because of the flowing movement of the sample which inhibits the polarization of the cathode which is necessary for successful operation.

Also, it is well-known that polarography using a dropping mercury cathode is suceptible to interference by any dissolved oxygen in the sample. Conventionally oxygen is removed by purging the sample with oxygen-free nitrogen gas prior to analysis, the flow of nitrogen being halted before analysis is begun to allow the sample to assume a stationary state. In flowing samples it is necessary, because fresh oxygen-containing sample is being constantly delivered to the analysis cell, to provide for continuous removal of a dissolved oxygen.

A previous proposal of the inventors of the present invention was the provision in a polarographic analysis cell for flowing samples, an inert gas diffuser in the analysis cell which delivered inert gas, normally nitrogen, continuously during analysis. The effect of turbulence caused by the diffused gas bubbles on the analytical result was reduced by providing a shield around the end of the dropping mercury cathode. This shield had the form of a funnel with an upper cup portion and a lower stem portion. The stem portion was a straight pipe of which the lower end opening was directed vertically downward toward the base of the cell. While this arrangement produced results hitherto unobtainable further research has produced a greatly improved configuration which is the subject of this present invention.

Accordingly the present invention provides apparatus for use in the continuous polarographic analysis of a flowing stream of liquid including, a cell having a floor, liquid inlet means opening into the cell above the floor and liquid outlet means located above the said inlet means;

means connected to the inlet means for effecting flow of liquid to be analysed through the cell;

a dropping mercury cathode extending into the cell, said cathode having an end portion terminating in a mercury-discharge tip directed towards said floor;

a gas diffuser located within the cell in the vicinity of said floor;

an open-ended tubular cathode shield surrounding the end portion of the cathode and located in the cell at a level intermediate the said inlet and outlet means, said shield having an upper cup portion and a lower stem portion, means on the stem portion defining a laterally-directed terminal orifice, said orifice having a cross-sectional area less than that of the stem portion;

support means for said shield and said cathode, said support means permitting relative displacement of the shield and cathode whereby the extent of insertion of the cathode end portion into the shield is adjustable; means supplying mercury to the cathode and discharging used mercury from the cell;

an anode within the cell; and electrical conductor means associated with said anode and cathode.

The means on the stem portion of the shield defining the terminal laterally directed orifice may be provided by a tapered and laterally curved end portion on the stem portion of the shield.

To permit the insertion of the dropping mercury electrode the internal dimensions of the stem are such as to permit insertion of the electrode thereinto to form a through-passage between the electrode and the internal surface of the stem portion.

Preferably both the cell and the shield are made of glass.

In analysing a stream of liquid by polarography utilising this apparatus a stream of solution is passed through the cell described above, part of the stream of liquid passing through a passage formed between the electrode and the shield, and the stream is polarographically analysed in said passage.

The apparatus of the invention obviously requires the use of auxiliary equipment. However, the invention provides within the flow cell a zone surrounding the mercury discharge tip of the cathode wherein the rate of flow of the stream of solution is smooth and constant. Solution flowing into the cell creates a zone of turbulence but part of the solution passes from the tubulent zone into the passage between electrode and shield in which the flow is smooth and constant and in which is located the mercury discharge tip of the capillary tube of the dropping mercury electrode. It is in this zone of smooth and constant flow that the polarographic analysis is carried out.

In common with normal polarographic analysis it is desirable that dissolved oxygen be removed from the solution prior to analysis. The invention therefore also includes means for de-aerating the solution in the cell during analysis and may optionally include means for de-aerating the sample prior to passage into the cell.

The apparatus includes a gas diffuser in the cell and this is conveniently a sintered glass plate which can disperse the gas into a fine cloud of bubbles.

One preferred form of continuous de-aerator for use prior to the cell comprises a glass coil through which the stream of solution is passed and is mixed with oxygen-free nitrogen. As the solution passes through the coil the dissolved oxygen is purged from the solution by the nitrogen gas. As the stream of solution containing bubbles of nitrogen passes into the flow cell the bubbles are allowed to escape.

While analysis by polarography is relatively free of interference by ions other than those to be determined, there are some ions which will interfere with the analytical result, for example, the cyanide ion. When such an ion is present in the sample it is preferred to mask its effect by reacting it with a complexing agent prior to passage into the cell. In the case of the cyanide ion, formaldehyde may be used as the complexing agent. To remove or minimise interference by ferric ions they may be reduced to the less interfering ferrous ion by means of ascorbic acid. Also it is sometimes necessary to treat the solution to be analysed with other chemical reagents such as buffer solutions and means may be provided in the apparatus for so doing.

An embodiment of the invention will now be described by way of illustration with reference to the accompanying drawing which shows apparatus of this invention, in partial section with associated auxiliary equipment shown schematically.

An apparatus of the present invention for use in polarographic analysis has a flow cell 1 with a mercury outlet 2. The cell has an inlet 3 and outlet 4 means for throughflow of liquid to be analysed. Generally centrally in the cell 1 there is provided a shield 5 for a dropping mercury cathode 6. The shield 5 has the shape of a funnel having a wide cup-shaped portion 7 and a narrow stem portion 8 extending from the cup 7.

Support 9 is provided for the cathode 6, a rod 10 attached to the cup portion 7 and associated mounting 11 for mounting the shield 5 within the cell 1 being also provided, said support 9 and mounting 11 being adjustable permitting relative longitudinal adjustment of the cathode in the shield 5. The shield 5 is mounted within the cell 1 in a vertical position with the wide cup-shaped portion uppermost. A lower portion 12 of the stem portion 8 is curved and tapered and terminates in a laterally directed orifice 13. This arrangement improves the flow characteristics of liquid through the stem and also prevents entry of bubbles of gas into the stem.

A gas diffuser 14 is provided in the cell, de-oxygenating inert gas being supplied through a pipe 15 which terminates in a sintered glass diffusing disc 16 near the floor of the cell.

The dropping mercury cathode 6 is mounted generally centrally within the cell 1 and extends into the shield 5, the lower end of the electrode extending slightly into the stem portion 8. Support means 9 permit raising and lowering of the dropping mercury cathode to increase or decrease the depth of the penetration of the electrode into the shield 5.

The mercury outlet 2 is located at or near the base of the cell 1 and comprises a conduit extending from the cell and having an inverted U bend so as to maintain a pool of mercury in the cell while at the same time permitting outflow of excess mercury from the cell.

An anode 30 is provided. In the embodiment illustrated in the drawing this is a glass tube 31 with a sealed-in platinum wire 32.

A standard reference electrode such as a standard calomel electrode, indicated by part 33 on the drawing, is also provided.

Liquid is supplied to the flow cell via the inlet 3 at or near its floor and liquid flows from the cell via the outlet 4 located in an upper portion of the cell. The liquid may be supplied to the cell by means of a peristaltic pump 17, which ensures a substantially constant flow rate to the cell.

A de-aerator 18 is provided, having the form of a helically coiled glass tube and has means 19 for introducing deoxygenating gas such as nitrogen into the coil in admixture with the liquid so as to remove oxygen.

Also, means 20 are provided for dosing chemical reagents such as masking agents and buffer solutions into the flowing sample.

A mercury reservoir 21 which is height-adjustable permitting adjustment of the drop rate of the mercury cathode is provided and is connected to the capillary dropping tube 6 by means of a flexible tube 22. Electrical conductors 23 for the cathode, 24 for the anode and 34 for the standard calomel electrode are provided.

A gas effluent duct 28 permits escape of gas via gas-trap 29. The cell is closed by a lid 27 which is apertured to permit passage of parts 6, 10, 15, 28, 30 and 33 therethrough.

Normal liquid level in the cell is indicated by line 25 and mercury level by line 26.

In use, a sample as withdrawn from a stream of liquid to be analysed by means of the peristaltic pump 17 and is passed upward through the vertically mounted helical tube deaerator 18, oxygenfree nitrogen being introduced at the lower end of the helically coiled tube 18 via a side arm 19. The effect of the nitrogen is to purge dissolved oxygen from the solution into the gaseous phase. The liquid, containing bubbles of nitrogen, is led from the top of the coil 18 to the inlet 3 of the flow cell 1 and the bubbles are allowed to escape from the cell preferably via a gas trap 28. The apparatus also includes means for mixing the liquid in the cell. Such means include the gas bubble disperser 14 located in the cell. This disperser also provides additional deaeration off the cell contents. If the sample is known to contain an interfering ion a masking agent may be introduced into the stream at any point, for example via a side arm 20, prior to the sample reaching the flow cell 1. The introduction of the masking agent may be effected by use of a second peristaltic pump which delivers the masking agent at a constant preset rate into the flowing stream of liquid.

The shield 5 is mounted in the flow cell in such a way that the lower curved end 12 of the stem 8 is directed away from the sample inlet. As the sample flows through the cell a portion thereof passes through the cup portion 7 of the shield 5 such flow being sufficient to ensure that the portion of sample in the shield is representative of the main body of liquid.

The dropping mercury cathode 6 is lowered centrally into the shield 5 so that its end just enters the stem portion 8. The dropping mercury cathode 6 may be raised or lowered in the stem portion 8 by means of adjustable mounting 9 to obtain a smooth flow of liquid through the shield. When the end of the dropping mercury cathode 6 enters the stem 8 a narrow passageway is formed between the outer wall of the cathode 6 and the inner wall of the stem 8. There is created within the shield 5 and around the end of the cathode 6 a zone in which there is a very smooth flow of liquid in which zone the polarographic determination may be carried out.

While the dimensions of the shield and electrode are not critical there are of course optimum relative values therefor. In determining such optimum values there are two factors to be borne in mind namely, (1), the internal diameter of the shield should be such as to permit free fall of drops of mercury from the electrode, and (2) the external diameter of the electrode relative to the internal diameter of the stem and the depth of penetration of the electrode into the stem should be chosen in conjunction with the current measurements from the electrode; the optimum values will be those which result in a steady current output from the electrode.

One particularly preferred form of the cathode shield 5 is one which is constructed from borosilicate glass. The upper cup-shaped portion 7 of the shield may be one centimeter in diameter and 0.75 centimeter in depth; the cupshaped portion narrows to join a stem portion which may be 0.32 centimeter in diameter and 2.0 centimeters long. The stem portion 8 is curved slightly at the lower end 12 to prevent gas bubbles entering the shield 5. The dropping mercury cathode is positioned in the shield such that the gap between the cathode and the stem portion is approximately 0.5 millimeter. A shield of dimensions mentioned above is a compromise between too large a diameter which results in erratic liquid flow and too small a diameter which impedes mercury flow. The dimensions represent relative sizes but they are not, of course, the only sizes which will function satisfactorily.

The cell provides for continuous flow of liquid therethrough and removal of waste mercury therefrom, but the cell geometry is not critical; any cell which fulfils these purposes can be used. A reference electrode, and an auxiliary electrode may also be used in conjunction with the apparatus of this invention.

We claim:

1. Apparatus for use in the continuous polarographic analysis of a flowing stream of liquid including, a cell having a floor, liquid inlet means opening into the cell above the floor and liquid outlet means located above the said inlet means;

means connected to the inlet means for effecting flow of liquid to be analysed through the cell;

a dropping mercury cathode extending into the cell, said cathode having an end portion terminating in a mercury-discharge tip directed towards said floor;

an open-ended tubular cathode shield surrounding the end portion of the cathode and located in the cell at a level intermediate the said inlet and outlet means, said shield having an upper cup portion and a lower stem portion, means on the stem portion defining a laterally-directed terminal orifice, said orifice having a cross-sectional area less than that of the stem portion;

support means for said shield and said cathode, said support means permitting relative displacement of the shield and cathode whereby the extent of insertion of the cathode end portion into the shield is adjustable;

means supplying mercury to the cathode and discharging used mercury from the cell; and anode within the cell; and electrical conductor means associated with said anode and cathode.

2. Apparatus as claimed in claim 1, wherein said means defining a laterally-directed terminal orifice on the stem portion is a tapered and laterally curved end portion of the stem portion.

3. Apparatus according to claim 2, including means for introducing a chemical reagent into the liquid prior to passage of the liquid into the cell.

4. Apparatus according to claim 1 in which means for deaerating liquid prior to passage of the liquid into the cell are provided.

5. Apparatus according to claim 4, including means for introducing a chemical reagent into the liquid prior to passage of the liquid into the cell.

6. Apparatus according to claim 1 in which a peristaltic pump provides the means for effecting flow of liquid through the cell.

7. Apparatus according to claim 6, including means for introducing a chemical reagent into the liquid prior to passage of the liquid into the cell.

8. Apparatus according to claim 1, including means for introducing a chemical reagent into the liquid prior to passage of the liquid into the cell.

9. Apparatus according to claim 1, in which the shield is of circular cross-section throughout, the cup portion has a diameter of 0.75 centimeters and the stem portion an internal bore of 0.32 centimeters, the dropping mercury cathode having an external diameter of 0.315 centimeters thus forming a gap between cathode and shield of 0.5 mm, and the overall length of the shield is 2.0 centimeters.

* * * * *